(12) United States Patent
Halsey

(10) Patent No.: US 6,620,982 B1
(45) Date of Patent: Sep. 16, 2003

(54) METHOD OF PRODUCING PURIFIED CYCLOPENTANE

(75) Inventor: Richard B. Halsey, Houston, TX (US)

(73) Assignee: Equistar Chemicals, LP, Houston, TX (US)

( * ) Notice: Subject to any disclaimer, the term of this patent is extended or adjusted under 35 U.S.C. 154(b) by 359 days.

(21) Appl. No.: 09/168,979

(22) Filed: Oct. 7, 1998

(51) Int. Cl.$^7$ ................................. C07C 5/02
(52) U.S. Cl. ........................... 585/264; 585/20
(58) Field of Search .................. 585/20, 264

(56) References Cited

U.S. PATENT DOCUMENTS

| | | | |
|---|---|---|---|
| 2,403,281 A | 7/1946 | Hill et al. ............ 260/666 |
| 2,412,936 A | 12/1946 | Hepp ................. 260/666 |
| 2,459,403 A | 1/1949 | Ahrens .............. 202/39.5 |
| 2,463,036 A | 3/1949 | Hervert et al. ........ 260/666 |
| 2,517,839 A | 8/1950 | Carnell ............... 260/666 |
| 2,530,727 A | 11/1950 | Ray .................. 260/666 |
| 3,344,198 A | 9/1967 | Weitz et al. .......... 260/666 |
| 3,655,806 A | 4/1972 | Brandt et al. ........ 260/681.5 |
| 3,686,349 A | 8/1972 | Schliebs et al. ...... 260/681.5 |
| 3,763,254 A | * 10/1973 | Engelhard et al. ...... 585/256 |
| 3,810,831 A | 5/1974 | Schleppinghoff et al. ... 208/321 |
| 3,853,748 A | 12/1974 | Tabler ................ 208/255 |
| 3,857,894 A | 12/1974 | Morelli et al. ........ 260/666 A |
| 3,947,510 A | 3/1976 | Morelli et al. ........ 260/677 H |
| 3,949,011 A | 4/1976 | Smirnov et al. ....... 260/666 A |
| 4,048,242 A | 9/1977 | Lauer et al. .......... 260/666 A |
| 4,271,323 A | 6/1981 | Durand et al. ........ 568/816 |
| 4,361,422 A | * 11/1982 | Derrien et al. ........ 44/56 |
| 4,648,959 A | * 3/1987 | Herber et al. ......... 208/89 |
| 4,849,566 A | * 7/1989 | Venier et al. ......... 585/23 |
| 4,990,710 A | 2/1991 | Dessau et al. ........ 585/277 |
| 5,012,022 A | * 4/1991 | Venier et al. ......... 585/20 |
| 5,192,728 A | 3/1993 | Dessau et al. ........ 502/66 |
| 5,283,385 A | 2/1994 | Dessau ............... 585/317 |
| 5,284,986 A | 2/1994 | Dessau ............... 585/318 |
| 5,352,846 A | * 10/1994 | Sarrazin et al. ...... 568/697 |
| 5,631,291 A | * 5/1997 | Mittendorf et al. .... 514/561 |

FOREIGN PATENT DOCUMENTS

DE  0 799 881  * 4/1997

OTHER PUBLICATIONS abstact of EP 0 799 881, Heners et al. Apr. 1997.*

* cited by examiner

Primary Examiner—Nadine G. Norton
(74) Attorney, Agent, or Firm—Jonathan L. Schuchardt

(57) ABSTRACT

A process for producing cyclopentane from by-product streams containing cyclopentene consists of distilling the cyclopentene from the feedstream and then hydrotreating the cyclopentene-containing fraction to cyclopentane. A second distillation step may then be employed to remove the hydrocarbons which are lighter than cyclopentane. The process has particular applicability in the treatment of feedstreams containing neo-hexane. The cyclopentene is easily separated from the neo-hexane in a conventional fractionator.

10 Claims, 1 Drawing Sheet

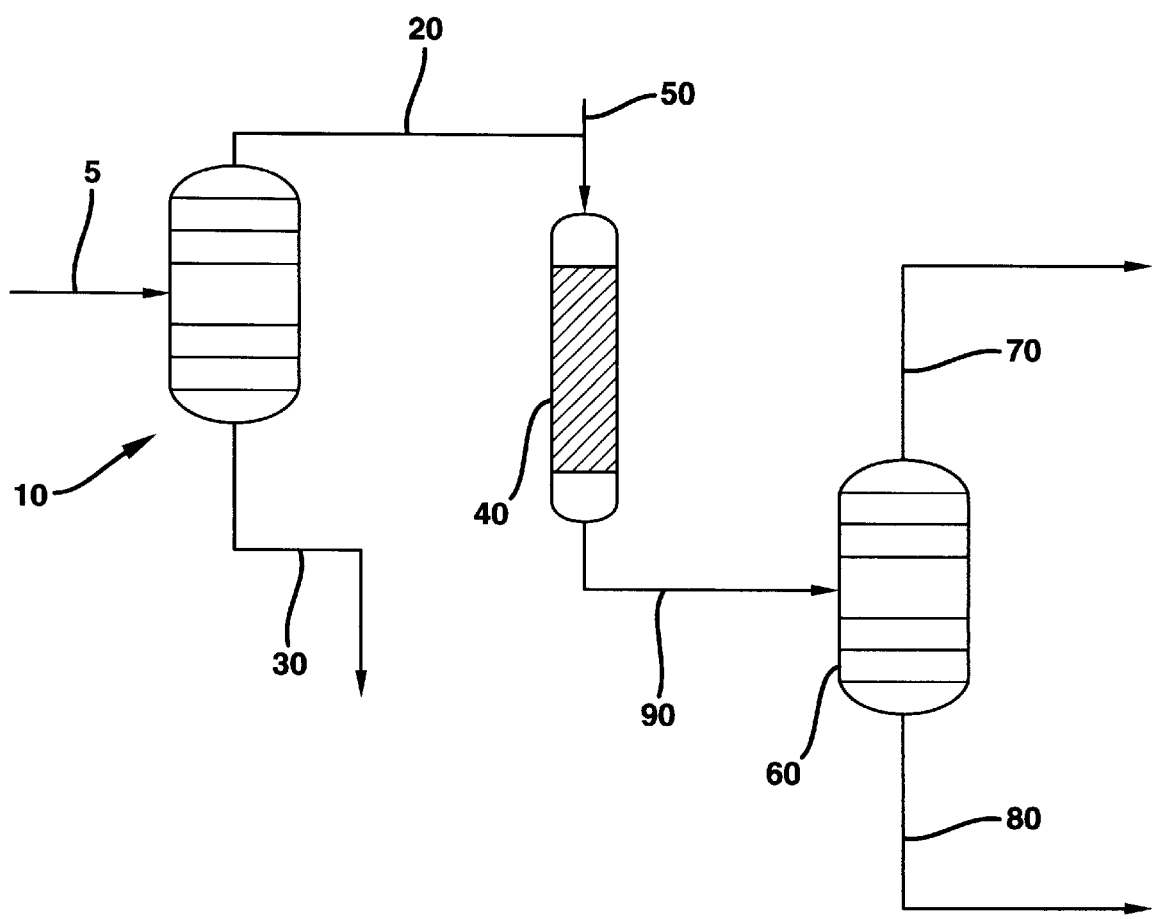

METHOD OF PRODUCING PURIFIED CYCLOPENTANE

FIELD OF THE INVENTION

This invention relates to a process for producing purified cyclopentane from a feedstream containing cyclopentene and, optionally, neo-hexane. In a preferred embodiment, the invention relates to a process wherein a cyclopentene containing fraction and a neohexane containing fraction are separated from a hydrocarbon stream, the cyclopentene containing fraction further containing other chemical constituents. The cyclopentene containing fraction is subjected to hydrotreatment. Purified cyclopentane is separated from the hydrotreated stream.

BACKGROUND OF THE INVENTION

Cyclopentane with a purity greater than 85% is a desirable product for solvents and polyurethane foaming agents. In addition, such cyclopentene may be used as a replacement for fluorocarbon refrigerants.

Typically, cyclopentane is recovered by fractionating natural gasoline at concentrations as low as 1.6 weight percent cyclopentane. It is difficult to process high purity cyclopentane from this process, however, since the contaminant neo-hexane has a boiling point very close to cyclopentane. While the boiling point of cyclopentene is about 111° F., the boiling point of cyclopentane is approximately 120.7° F. The boiling point of neo-hexane is approximately 121.5° F. Thus, it is difficult to separate cyclopentane and neo-hexane efficiently. In fact, a practical maximum concentration of only 80 weight percent is possible from such fractionation processes. Further, such processes are both energy and capital intensive.

Cyclopentane can also be produced by backcracking dicyclopentadiene (DCPD) to cyclopentadiene. Cyclopentadiene is then hydrotreated to cyclopentane. This procedure, however, requires a backcracking reactor, a hydrotreater, and a post-fractionation unit. In addition, backcracking DCPD and converting it to cyclopentane has several negative factors. First, the backcracking reaction is highly endothermic, thereby requiring a fired heater. Second, low quality by-product DCPD streams have high value in the resin market. Thus, it is cost inefficient to use the DCPD as a feedstream. Third, hydrotreating cyclopentadiene requires large amounts of hydrogen at high capital costs.

A process for producing cyclopentane of high purity is therefore desired which avoids the problems of the prior art.

SUMMARY OF THE INVENTION

A process for producing cyclopentane from by-product streams containing cyclopentene consists of distilling the cyclopentene from the feedstream and then hydrotreating the cyclopentene-containing fraction to cyclopentane. A second distillation step may be employed to remove the hydrocarbons which are lighter than cyclopentane. In a preferred embodiment, the process consists of preparation of a purified cyclopentane stream from an impure cyclopentene containing fraction wherein the impure cyclopentene containing fraction is subjected to hydrotreatment.

The feedstream may be a by-product stream, such as one containing piperylene resins, or one from a delayed coking reactor as well as a stream from coal liquefication. In a preferred embodiment, the feedstream is obtained by steam cracking of olefins.

The process of the invention offers several advantages over the prior art. First, it permits the efficient removal of cyclopentene from a feedstream containing neo-hexane, also known as 2,2-dimethylbutane, since there is a 10° temperature difference between cyclopentene and, when present, neo-hexane. Second, the process permits conventional distillation equipment and conditions to be used. Third, the hydrotreatment of the cyclopentene containing fraction to cyclopentane uses a minimum amount of hydrogen. Lastly, the final distillation step permits the removal of cyclopentane from the remaining contaminants, such as linear and branched olefins, which have a lower boiling point than cyclopentane.

BRIEF DESCRIPTION OF THE DRAWINGS

The FIGURE is a schematic illustration of the process of the invention.

DETAILED DESCRIPTION OF PREFERRED EMBODIMENTS

A hydrocarbon stream containing cyclopentene is treated in accordance with the process of the invention in order to separate cyclopentene from other chemical species. The cyclopentene-containing fraction is then hydrotreated to obtain purified cyclopentane.

Typically, the cyclopentene-containing feedstream can be a hydrocarbon stream from an olefin steam cracking unit, a stream from a delayed coker, a stream from coal liquefication or a byproduct stream containing piperylene resins. The process of the invention may be used on any feedstream containing cyclopentene.

The invention has particular applicability in the treatment of feedstreams containing neo-hexane. The cyclopentene is easily separated from neo-hexane in a conventional fractionator as an overhead product. In particular, the invention renders excellent results when the concentration of cyclopentene is at least 25 weight percent in the feedstream.

As set forth in FIGURE feedstream 5 is fed into distillation column 10. Temperatures within the distillation column are between 120° F. to about 170° F. In the fractionator, the cyclopentene is separated from neo-hexane as an overhead product 20. The cyclopentene stream is not a purified stream but rather contains a number of impurities. For instance, the cyclopentene typically further contains other four and five carbon membered straight chain and/or branched chain hydrocarbons which may or may not contain double bonds. Neo-hexane leaves the column as the high temperature boiling bottoms product 30.

Where the hydrocarbon stream is obtained by steam cracking olefins, the cyclopentene containing fraction will likely contain pentane as well as 2-pentene and further 2-methyl-2-butene. For instance, the cyclopentene containing fraction may be one composed of the components set forth in Table 1 (mol percentages approximate):

TABLE 1

| Component | Mol % |
| --- | --- |
| Isobutane | 0.31 |
| Isobutene | 0.54 |
| Butene-1 | 0.61 |
| Isopentane | 0.11 |
| 2-Methyl-1-Butene | 0.08 |
| Pentane | 20.26 |
| Trans-2-Pentene | 8.82 |

TABLE 1-continued

| Component | Mol % |
|---|---|
| Cis-2-Pentene | 7.48 |
| 2-Methyl 2-Butene | 4.25 |
| 1,3-Cyclopentadiene | 0.28 |
| Trans-1,3-Pentadiene | 0.89 |
| Cis-1,3-Pentadiene | 0.89 |
| Cyclopentene | 55.41 |
| 1,2 Pentadiene | 0.07 |

The cyclopentene containing fraction is then introduced to hydrotreater 40 along with hydrogen 50. In hydrotreater 40, the cyclopentene fraction is converted to higher boiling cyclopentane and other mixed four and five carbon membered straight chain or branched chain hydrocarbons by hydrotreating the stream over a catalyst. In essence, cyclopentene and the other components of the cyclopentene containing fraction are hydrogenated in the hydrotreater. This facilitates the separation of purified cyclopentane from the other components, now hydrogenated, from the cyclopentene containing fraction. This is the case since the boiling point of cyclopentane is more clearly defined over the boiling point of the other saturated components in the hydrotreated stream than prior to hydrotreatment.

Typically, catalysts which may be employed in hydrotreater 40 include nickel molybdenum, cobalt molybdenum or another nickel containing catalyst. Further, the catalyst is typically supported on a catalyst bed, such as alumina. Exemplary of acceptable catalysts is Shell 424 nickel molybdenum catalyst, a product of the Shell Oil Company, over an alumina bed. The temperature in hydrotreater 40 is generally about 350° F. to about 600° F., preferably about 400° F. to about 450° F. The pressure in the hydrotreater 40 is generally about 100 psig to about 1,000 psig, preferably about 250 to about 500 psig. The ratio of hydrogen to the cyclopentene fraction is between about 900 to about 2,000 standard cubic feet (scf))/barrel, preferably between about 1,000 to about 1,500 scf/b.

The hydrotreated product 90 is then introduced into a second distillation column 60. The temperatures are typically between 100° F. to 170° F. This second distillation removes low temperature boiling contaminant components as distillate as top fraction 70. Such contaminants include the four and five membered saturated carbon compounds. The remaining bottoms product 80 is high-purity cyclopentane. Unconverted cyclopentene from hydrotreater 40 has a lower boiling point than cyclopentane and thus also leaves second distillation column 60 as overhead product 70.

The following example will illustrate the practice of the present invention in a preferred embodiments. Other embodiments within the scope of the claims herein will be apparent to one skilled in the art from consideration of the specification and practice of the invention as disclosed herein. It is intended that the specification, together with the example, be considered exemplary only, with the scope and spirit of the invention being indicated by the claims which follow.

EXAMPLE

This Example illustrates the production of cyclopentane from a mixed olefins stream containing cyclopentene and neo-hexane. The stream is first distilled to separate the cyclopentene from neo-hexane. Feed to the distillation column typically contains about 26 mole percent cyclopentene and 21 mole percent neo-hexane. The stream is separated in a distillation column containing 170 actual trays (120 theoretical trays) with a reflux to distillate product ratio of nine to one. The overhead pressure is 11 psig. The overhead product from the distillation column will be observed to contain 55.0 mole percent cyclopentene. The cyclopentene-containing fraction likely further contains the components set forth in Table 1 above.

The overhead product is then hydrotreated in a reactor containing Shell 424 catalyst using nickel and molybdenum on an alumina support. The hydrogen to feed ratio is 1000 scf of hydrogen to one barrel of feed. The liquid is fed to the reactor at the rate of two pounds of feed per hour for each pound of catalyst for a weight hourly space velocity of 2 hr. The reactor operating pressure is about 290 psig and the inlet temperature is 405° F. A complete conversion of cyclopentene to cyclopentane is observed.

The reaction product liquid is then separated from the hydrogen gas using a flash drum operating at 20 psig and 100° F. The liquid is distilled to remove hydrocarbon that boils in the range of cyclopentene and lighter. The liquid is sent to a column containing 57 actual trays (40 theoretical trays) with a reflux to distillate product ratio of seven to one. The overhead pressure is 11 psig. The bottoms product from the distillation column is observed to contain about 96.0 mole percent cyclopentane and 2.0 mole percent neo-hexane.

From the foregoing, it will be observed that numerous variations and modifications may be effected without departing from the true spirit and scope of the novel concepts of the invention.

What is claimed is:

1. A process which comprises:
   (a) distilling a hydrocarbon stream that contains neo-hexane, hydrocarbon impurities, and at least 25 wt % of cyclopentene to separate a neo-hexane-containing fraction from a lower-boiling fraction that contains cyclopentene and hydrocarbon impurities;
   (b) hydrogenating the lower-boiling fraction in the presence of a catalyst to produce a mixture of cyclopentane and saturated $C_4$–$C_5$ hydrocarbons; and
   (c) distilling the hydrogenated mixture to recover cyclopentane having a purity greater than 85 mol %.

2. The process of claim 1 wherein the hydrocarbon stream contains at least 20 mole % of neo-hexane.

3. The process of claim 1 wherein the hydrocarbon stream is obtained by steam cracking of olefins.

4. The process of claim 1 wherein distillation step (a) is performed at a temperature within the range of 120° F. to 170° F.

5. The process of claim 1 wherein the hydrogenation catalyst contains nickel, cobalt, or molybdenum.

6. The process of claim 1 wherein the hydrogenation catalyst is supported.

7. The process of claim 1 wherein the hydrogenation is performed at a temperature within the range of 350° F. to 600° F. and at a pressure within the range of 100 psig to 1000 psig.

8. The process of claim 1 wherein distillation step (c) is performed at a temperature within the range of 100° F. to 170° F.

9. The process of claim 1 wherein the recovered cyclopentane has a purity greater than 95 mol %.

10. A process which comprises:
    (a) distilling a hydrocarbon stream that contains at least 20 mole % of neo-hexane, hydrocarbon impurities, and at least 25 wt. % of cyclopentene at a temperature within the range of 120° F. to 170° F. to separate a neo-hexane-containing fraction from a lower-boiling fraction that contains cyclopentene and hydrocarbon impurities;

(b) hydrogenating the lower-boiling fraction in the presence of a supported nickel, cobalt, or molybdenum catalyst to produce a mixture of cyclopentane and saturated $C_4$–$C_5$ hydrocarbons; and (c) distilling the hydrogenated mixture at a temperature within the range of 100° F. to 170° F. to recover cyclopentane having a purity greater than 95 mol %.

* * * * *